(12) United States Patent
Dao et al.

(10) Patent No.: US 7,851,510 B2
(45) Date of Patent: Dec. 14, 2010

(54) GOSSYPOL DERIVATIVES, PRODUCTION METHOD THEREOF AND USES OF SAME

(75) Inventors: Vi-Thuy Dao, Antony (FR); Jean De Gunzburg, Paris (FR); Robert Michelot, Antony (FR); Oliver Christophe De Mil, Paris (FR)

(73) Assignees: Centre National de la Recherche Scientifique (C.N.R.S.), Paris (FR); Institut National de la Sante et de la Recherche Medicale (I.N.S.E.R.M), Paris (FR)

( * ) Notice: Subject to any disclaimer, the term of this patent is extended or adjusted under 35 U.S.C. 154(b) by 520 days.

(21) Appl. No.: 10/585,444

(22) PCT Filed: Jan. 6, 2005

(86) PCT No.: PCT/FR2005/000022

§ 371 (c)(1),
(2), (4) Date: Jun. 4, 2009

(87) PCT Pub. No.: WO2005/073158

PCT Pub. Date: Aug. 11, 2005

(65) Prior Publication Data

US 2009/0318566 A1     Dec. 24, 2009

(30) Foreign Application Priority Data

Jan. 8, 2004 (FR) ................................. 04 00125

(51) Int. Cl.
*A61K 31/225* (2006.01)
*A61K 31/11* (2006.01)
*A61K 31/70* (2006.01)
*A61K 31/122* (2006.01)
*C07C 50/32* (2006.01)
*C07C 321/06* (2006.01)
*A61P 35/00* (2006.01)
*A61P 37/00* (2006.01)

(52) U.S. Cl. .................... 514/682; 514/569; 514/681; 514/700; 514/548; 568/327; 568/43

(58) Field of Classification Search .................. None
See application file for complete search history.

(56) References Cited

U.S. PATENT DOCUMENTS 5,385,936 A    1/1995  Reidenberg et al.

FOREIGN PATENT DOCUMENTS

WO           01/00554       1/2001

OTHER PUBLICATIONS

Dao et al. New thioderivatives of gossypol and gossypolone, as prodrugs of cytotoxic agents. Bioorganic & Medicinal Chemistry, 11, 2003, 2001-2006.*
Haas et al. The oxidation of Gossypol. II. Formation of gossypolone with ferric chloride. J. Org. Chem. 30(12), pp. 4111-4113. 1965.*
V-T. Dao et al: "New thioderivatives of gossypol and gossypolone, as prodrugs of cytotoxic agents" Biooraganic and Medicinal Chemistry, vol. 11, 2003, pp. 2001-2006.
Dao V-T et al: "Synthesis and cytotoxicity of gossypol related compounds" Euorpean Journal of Medicinal Chemistry Editions Scientifique Elsvier, Paris, FR, vol. 35, No. 9, Sep. 2000, pp. 805-8013.

* cited by examiner

*Primary Examiner*—Brandon J Fetterolf
*Assistant Examiner*—Anna Pagonakis
(74) *Attorney, Agent, or Firm*—Young & Thompson

(57) ABSTRACT

The present invention relates to compounds of general formula (1):

(1)

[Chemical structure of formula (1) showing two linked naphthoquinone rings with substituents $R_1$, $R_2$, $R_5$, $R_6$, HO, and OH groups]

in which, independently of each other, $R_1$ and $R_2$ represent:
—OH, or
—$CH_2$—O—$R_3$, or
—$CH_2$—S—$R_3$, or $$-CH_2-N\begin{matrix}R_3\\R_4,\end{matrix}$$

$R_3$, $R_4$, $R_5$ and $R_6$ representing, independently of each other, —H or a carbon-containing group with 1 to 10 carbon atoms, saturated or unsaturated, optionally substituted with one or more heteroatomic groups.

The invention also relates to pharmaceutical compositions containing these compounds, and their uses, in particular in the context of the treatment of cancer.

10 Claims, No Drawings

GOSSYPOL DERIVATIVES, PRODUCTION METHOD THEREOF AND USES OF SAME

A subject of the present invention is gossypol derivatives, and more particularly reduced and oxidized derivatives of gossypolone, as well as the methods for obtaining them and their uses, in particular in pharmaceutical compositions intended for the treatment of cancers.

Gossypol is generally extracted from cotton plant seeds of the *Gossypium* genus (Malvaceae family). The content varies from 0.1 to 0.64% depending on the variety of *Gossypium* considered.

The first extraction of gossypol was carried out in a rudimentary fashion by Kuhlmann in 1861, he called the substance <<cotton-seed blue>>. In 1866, Longmore found that the oil of cotton seeds contains a coloured compound, isolated in the form of a brown solid and which is indisputably impure gossypol. It was not until 1899 that Marchlewski obtained the pure crystalline form, extracted from cotton seeds, which he called gossypol (Adams et al. (1960) *Chem. Rev.* 60:555-574).

Inspired by the works of their predecessors, Withers and Carruth, in 1915, significantly improved the extraction of gossypol and even today their method still remains one of the best methods used (Adams et al. (1960) *Chem. Rev.* 60:555-574).

The gossypol molecule is in the form of two symmetrical naphthalene sub-units, which are each substituted with three phenolic functions and an aldehyde function.

It exists in three tautomeric forms represented by the following formulae: aldehyde, hemiacetalic and quinone-methine forms. Its molar mass is: 518.5 g/mol ($C_{30}H_{30}O_8$).

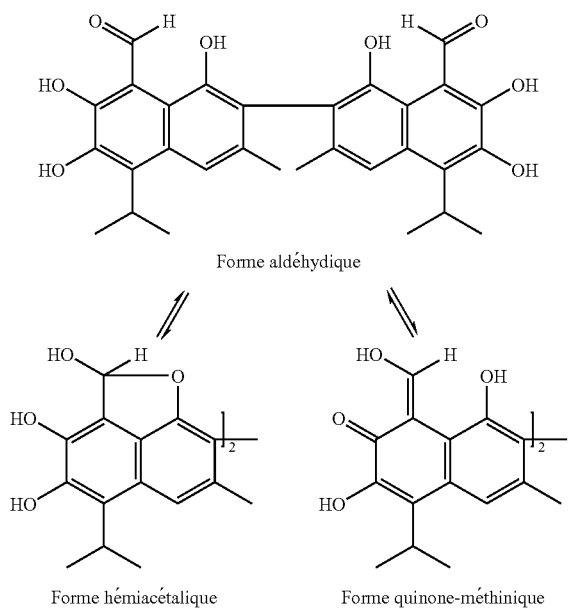

Analysis of the rotatory power of gossypol, revealed the presence of two isomers. The (+) gossypol is mainly found in the bark of Thephesia populnea and certain varieties of cotton plants (*Gossypium hirsutum*), while the levorotatory isomer (the (−) gossypol) is mostly found in other varieties of cotton plants such as *Gossypium barbadense* (Zhou & Lin (1988) *Contraception* 37:239-245; Cass et al. (1991) *Phytochemistry* 30:2655-2657).

The method used for measurement of the enantiomeric excess in the seeds of the different cotton plants is that which Matlin and Zhou applied using chiral Schiff bases of (+) or (−) gossypol carrying out their separation by HPLC (Zhou & Lin (1988) *Contraception* 37:239-245; Matlin et al. (1984) *Journal of High Resolution Chromatography and Chromatography Communication* 7:629-631; Fish et al. (1995) *Tetrahedron asymmetry* 6:873-876).

Gossypolone is obtained by oxidation of gossypol. For this purpose the production method described by Hass & Shirley (1965) *J. Org. Chem.* 30:4111-4113, using ferric chloride is the most common.

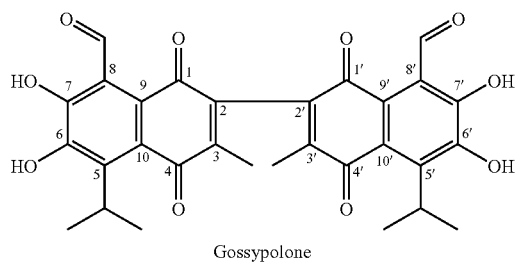

Gossypolone

Gossypol has numerous biological activities, which is shared to a certain degree by its derivatives. Although it was initially studied principally for its contraceptive or antiparasitic properties (against viruses or protozoans), it is its antitumour activities which now interest doctors. As its toxicity at high doses is not insignificant and leads to multiple side effects in humans, the research is directed at derivatives more specifically targeting the cancer cells.

The large amount of bibliographical data on the activities of gossypol derivatives indicates that the activity is associated with the presence on the binaphthalene system of the free phenolic groups in position 6,6' and 7,7'. In fact, blocking these phenol functions, in methoxyether derivatives, removes any toxicity. The toxicity of gossypol is also associated with the aldehyde functions or with the presence of an electrophilic function such as an enamine in the same position. It can be easily supposed that this electrophilic centre can link with a number of nucleophilic entities playing an important role in the biological environment. For example, the amine groups of the lysine of the proteins or of the peptides couple easily with gossypol.

To this end, the article by Dao et al. (2003) *Bioorg. Med. Chem.* 11:2001-2006 describes dithiolane and dithiane derivatives of gossypol and gossypolone, having a cytotoxicity less than that of gossypol and of gossypolone on the KB cell line. These derivatives are, moreover, capable of being modified on contact with nitronium ions, which are preferably present in certain tumours, into highly cytotoxic compounds. These compounds therefore do not act directly.

The purpose of the present invention is to provide new derivatives of gossypolone having a cytotoxicity less than or equal to that of gossypol and gossypolone, causing fewer side effects than gossypol and gossypolone, and capable of directly inhibiting protein kinases which can be involved in the development and maintenance of tumours.

The purpose of the invention is also to provide new synthesis methods for the above-mentioned derivatives.

The purpose of the invention is also to provide new pharmaceutical compositions, comprising the derivatives of the invention, and the use of said compositions in the context of the treatment of cancer, these compositions having the advantage of not being toxic at the doses used for the organism, and of specifically inhibiting certain protein kinases which can be involved in the growth of cancer cells.

The present invention relates to compounds of general formula (1):

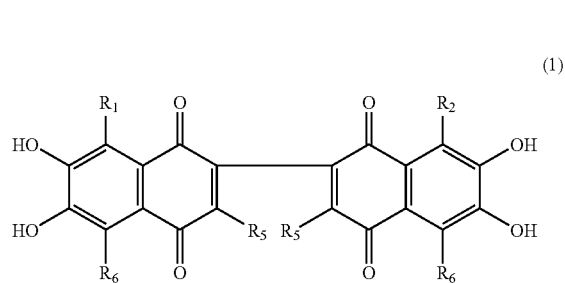

(1)

in which, independently of each other, $R_1$ and $R_2$ represent:
—OH, or
—$CH_2$—O—$R_3$, or
—$CH_2$—S—$R_3$, or

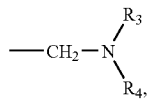

$R_3$, $R_4$, $R_5$ and $R_6$ representing, independently of each other, —H or a carbon-containing group with 1 to 10 carbon atoms, saturated or unsaturated, optionally comprising one or more heteroatomic groups.

<<Heteroatomic group>> refers to a group comprising at least one heteroatom, such as O, N, S, P, Cl, Br, F or I, said group for example being able to correspond to —OH, —$NH_2$, —SH.

According to a particular embodiment, independently of each other, $R_3$, $R_4$, $R_5$ and $R_6$ represent:
—H, an alkyl group, a heteroalkyl group, such as a thioalkyl, a hydroxyalkyl, an aminoalkyl, a halogenoalkyl or an alkoxyalkyl, a cycloalkyl group, an alkenyl group, a heteroalkenyl group, an aryl group, a heteroaryl group, such as a thioaryl, a hydroxyaryl, an aminoaryl, a halogenoaryl or an alkoxyaryl, or an arylalkyl group.

According to a preferred embodiment $R_3$, $R_4$, $R_5$ and $R_6$ comprise, independently of each other, from 1 to 8 carbon atoms.

According to another particular embodiment, $R_5$ and $R_6$, independently of each other, represent an alkyl group with 1 to 8 carbon atoms.

According to another particular embodiment, $R_1$ and $R_2$ are identical.

According to another particular embodiment, $R_5$ represents a methyl group and $R_6$ represents an isopropyl group.

According to another particular embodiment, $R_3$ represents —H or an alkyl or hydroxyalkyl group with 1 to 4 carbon atoms, or a benzyl group, if appropriate substituted with one or more alkyl or alkoxy groups with 1 to 4 carbon atoms, and/or by one or more halogen atoms.

According to a preferred embodiment the invention relates to compounds as defined above, of general formula (1a):

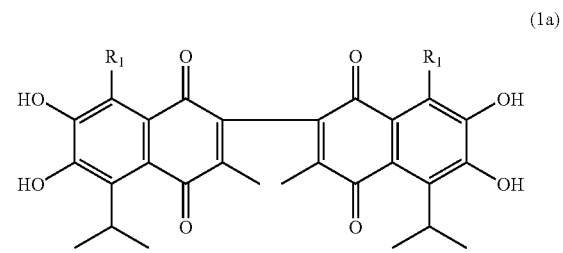

(1a)

in which $R_1$ represents:
—OH, or
—$CH_2$—O—$R_3$, or
—$CH_2$—S—$R_3$, $R_3$ being as defined above.

The invention in particular relates to compounds as defined above, of general formula (2):

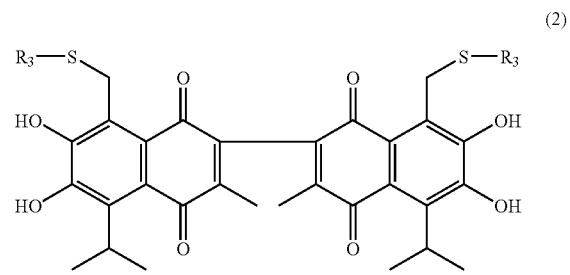

(2)

in which $R_3$ is as defined above.

The invention in particular relates to compounds as defined above, of general formula (3):

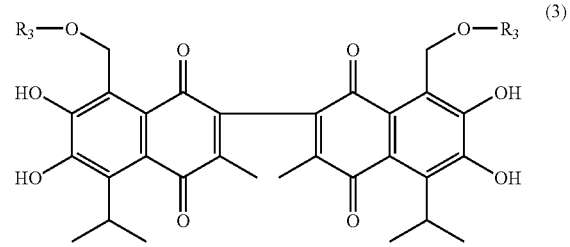

(3)

in which $R_3$ is as defined above.

The invention more particularly relates to compounds as defined above, of the following formula:

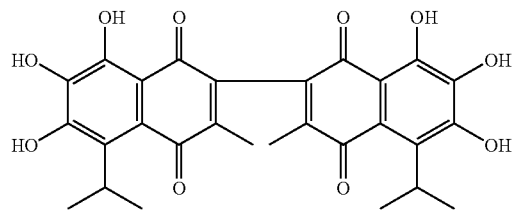
(4)
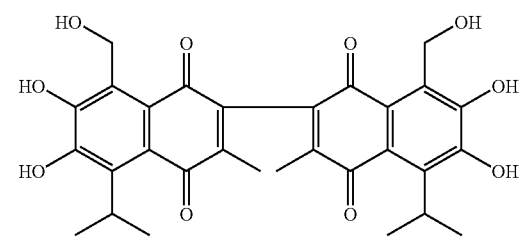
(5)
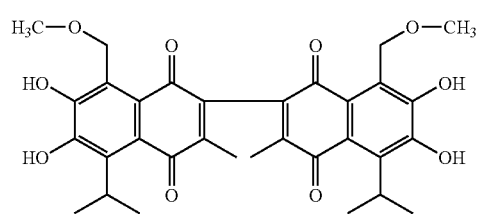
(6)
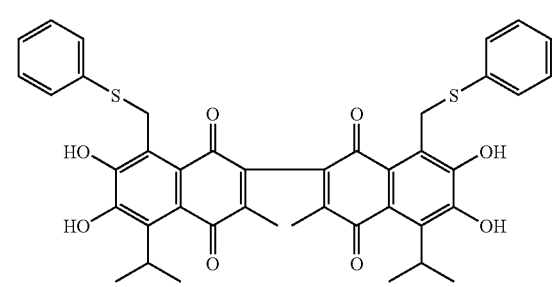
(7)
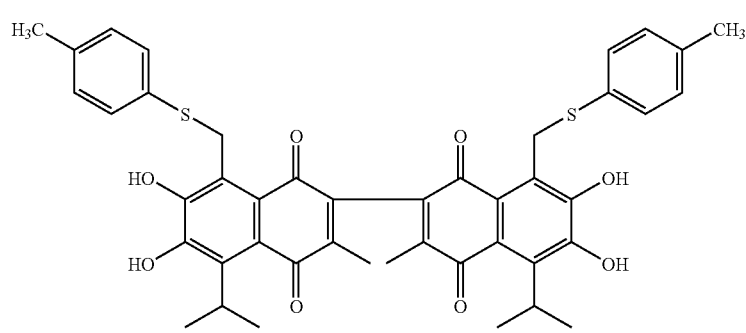
(8)
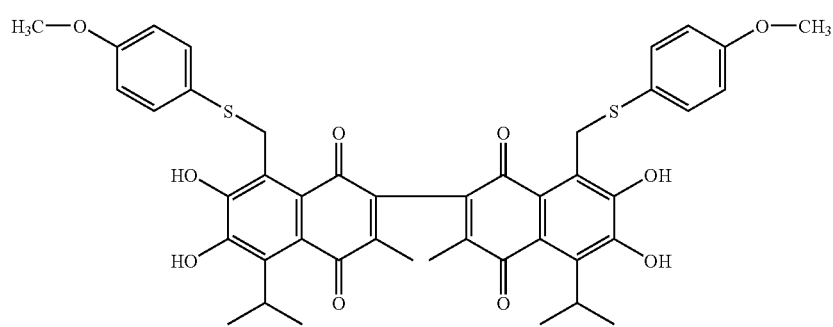
(9)
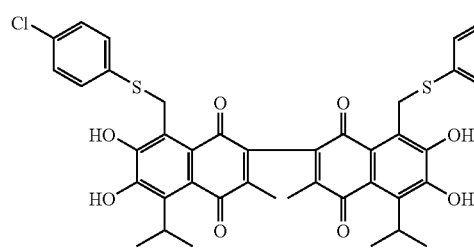
(10)
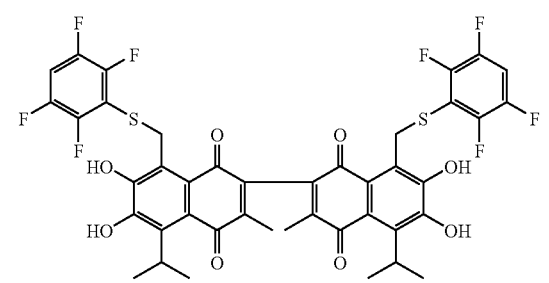
(11)
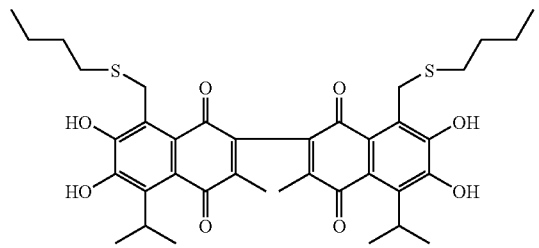
(12)
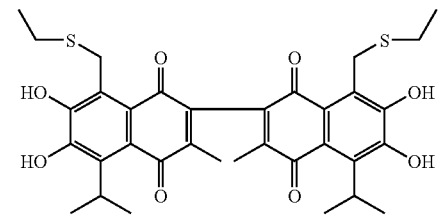
(13)

The present invention also relates to a pharmaceutical composition comprising as active ingredient at least one compound as defined above, or their pharmaceutically acceptable salts.

Such a composition is advantageous as it aims to inhibit protein kinases which can be involved in the development and/or maintenance of tumours, and causes fewer side effects than the pharmaceutical compositions containing gossypol and/or gossypolone.

According to particular embodiment the pharmaceutical composition comprises as active ingredient the compound (4) and/or the compound (14), as defined above.

The present invention also relates to the use of a compound as defined above, for the preparation of a medicament intended for the treatment of cancer, parasitoses, such as malaria, viroses or graft rejections, or for male contraception.

Parasitoses include in particular diseases of which the etiologic agent is a protozoan, such as *Plasmodium falciparum* for example.

The use of the compounds of the invention is advantageous since they are able to carry out therapeutic functions similar to those of gossypol and gossypolone while causing fewer side effects than gossypol and gossypolone.

According to a preferred embodiment, the compound (4) and/or the compound (14) as defined above, are used for the preparation of a medicament intended for the treatment of cancers, such as melanomas, colon cancers, lung cancers, glioblastomas, adenocarcinomas, prostate cancers or breast cancers.

The use of compounds (4) and (14) is advantageous since these compounds specifically and directly inhibit the activity of the SGK and PRAK kinases, which can be involved in the development and/or maintenance of tumours and cause fewer side effects than gossypol and gossypolone.

The present invention also relates to a method for the preparation of a compound of general formula (2) as defined above or a compound of formula (3) as defined above, characterized in that it comprises:
- a stage of reduction of the gossypolone in order to form the compound of formula (5) as defined above, and
- a stage of substitution of said compound of formula (5) with a compound of formula $R_3$—SH in order to form a compound of formula (2), or with a compound of formula $R_3$—OH in order to form a compound of formula (3).

The present invention also relates to a method for the preparation of a compound of general formula (4), as defined above, characterized in that it comprises a stage of oxidation of the gossypolone.

EXAMPLES

Example 1

Synthesis of an oxidized derivative of gossypolone, 6,7,8,6',7',8'-hexahydroxy-5,5'-diisopropyl-3,3'-dimethyl-[2.2']binaphthalenyl-1,4,1',4'-tetraone (4)

1 g of gossypolone (1.83 mmole) is dissolved in 50 ml of acetone and placed under argon, 8 ml of $H_2O_2$ 30% is added in 0.5 ml each time and stirred at ambient temperature. After 24 hours, the reaction, which is monitored by HPLC, is finished. The reaction mixture is washed with a concentrated solution of $FeSO_4$, then with saturated NaCl, dried over $Na_2SO_4$, and evaporated. The product is obtained by precipitation from ether and hexane.

Yield: 95%

Mass spectrometry (ESI): 521 (M–H)
IC50 (KB cell line)=$10^{-6}$ M.

The cytotoxicity of the compound vis-à-vis the KB tumour cell line was measured as is described in Dao et al. (2003) *Bioorg. Med. Chem.* 11:2001-2006.

The data for NMR $^1$H (on the left) and $^{13}$C (on the right) are shown in the formula (4):

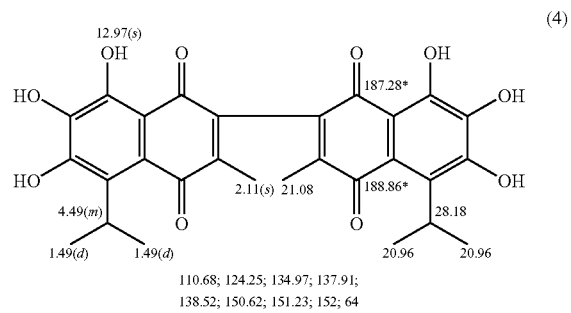

Example 2

Synthesis of a reduced derivative of gossypolone, 6,7,6',7'-tetrahydroxy-8,8'-bis-hydroxymethyl-5,5'-diisopropyl-3,3'-dimethyl-[2,2']binaphthalenyl-1,4,1',4'-tetraone (5)

1 g of gossypolone (1.83 mmole) and 4 mol. eqv. of $NaBH_3CN$ are added into 50 ml of methanol and placed under argon. Then, a 3N solution of HCl-MeOH (450 μl) is added dropwise for 5 min at 25° C. After 15 min, the reaction, monitored by HPLC, is finished. The reaction mixture is poured into a flask which contains 300 ml of 1N HCl and an orange precipitate forms. The residue separated and it is dissolved in ether, the ethereal phase is washed with water (3 times), then with saturated NaCl, dried over $Na_2SO_4$, and evaporated. The product is obtained by precipitation from ether and hexane.

Yield: 95%
Mass spectrometry (ESI): 573 (M+Na)
IC50 (KB cell line)=$10^{-6}$ M

The data for NMR $^1$H (on the left) and $^{13}$C (on the right) are shown in the formula (5):

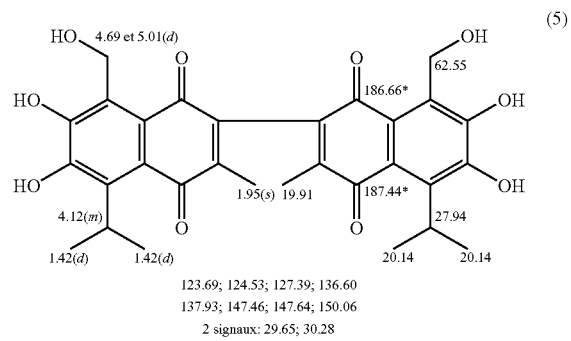

Example 3

Synthesis of a thioether derivative of the compound of formula (2), 6,7,6',7'-tetrahydroxy-5,5'-diisopropyl-3,3'-dimethyl-8,8'-bis-phenylsulphanylmethyl-[2,2']binaphthalenyl-1,4,1',4'-tetraone (7)

3 mol. eqv. of trifluoroacetic anhydride (TFAA) is added to a solution of 200 mg of the compound of formula (5) (0.36 mmole) in 10 ml of THF at 0° C. The mixture is stirred at 0° C. for 15 min. Then the mixture is evaporated in order to eliminate the THF. The reaction mixture is taken up in 10 ml of ether and 3 mol. eqv. of a monothiol, in this case benzenethiol, is added. After 24 hours, the reaction mixture is washed with 5% NaHCO$_3$ (3 times) and with water (3 times), then with saturated NaCl, dried over Na$_2$SO$_4$, and evaporated. The product is obtained by precipitation from ether and hexane.

Yield: 60-70%

Mass spectrometry (ESI): 733 (M−H)

IC50 (KB cell line)=4×10$^{-6}$ M

The data for NMR $^1$H (on the left) and $^{13}$C (on the right) are shown in the formula (7):

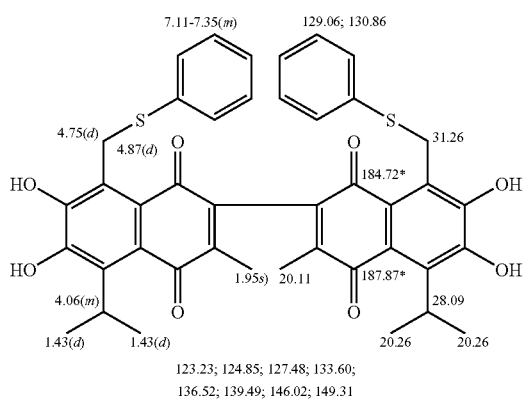

(7)

Example 4

Synthesis of 6,7,6',7'-tetrahydroxy-5,5'-diisopropyl-3,3'-dimethyl-8,8'-bis-p-tolylsulphanylmethyl-[2,2']binaphthalenyl-1,4,1',4'-tetraone (8)

The synthesis is essentially carried out as described in Example 3, the monothiol used being methylbenzenethiol.

Yield 60-70%

Mass spectrometry (ESI): 761 (M−H)

IC50 (KB cell line)=6.5×10$^{-6}$ M

The data for NMR $^1$H (on the left) and $^{13}$C (on the right) are shown in the formula (8):

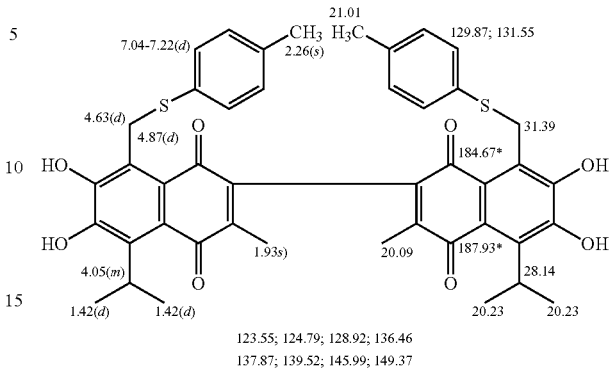

(8)

Example 5

Synthesis of 6,7,6',7'-tetrahydroxy-5,5'-diisopropyl-8,8'-bis-(4-methoxy-phenylsulphanylmethyl)-3,3'-dimethyl-[2,2']binaphthalenyl-1,4,1',4'-tetraone (9)

The synthesis is essentially carried out as described in Example 3, the monothiol used being methoxybenzenethiol.

Yield 60-70%

Mass spectrometry (ESI): 793 (M−H)

IC50 (KB cell line)=6.5×10$^{-6}$ M

The data for NMR $^1$H (on the left) and $^{13}$C (on the right) are shown in the formula (9):

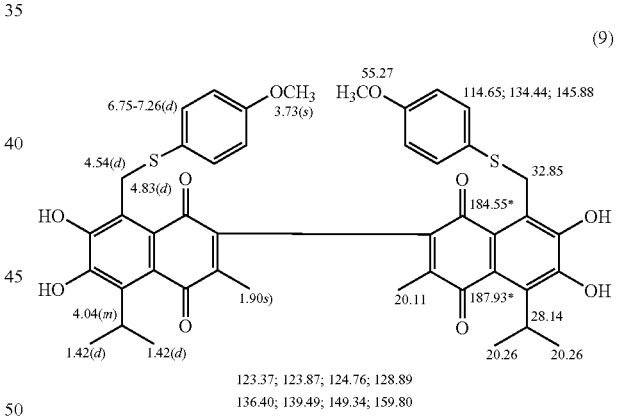

(9)

Example 6

Synthesis of 6,7,6',7'-tetrahydroxy-5,5'-diisopropyl-8,8'-bis-(4-chloro-phenylsulphanylmethyl)-3,3'-dimethyl-[2,2']binaphthalenyl-1,4,1',4'-tetraone (10)

The synthesis is essentially carried out as described in Example 3, the monothiol used being para-chlorobenzenethiol.

Yield 60-70%

Mass spectrometry (ESI): 802 (M−H)

IC50 (KB cell line)=3×10$^{-6}$ M

The data for NMR $^1$H (on the left) and $^{13}$C (on the right) are shown in the formula (10):

(10)

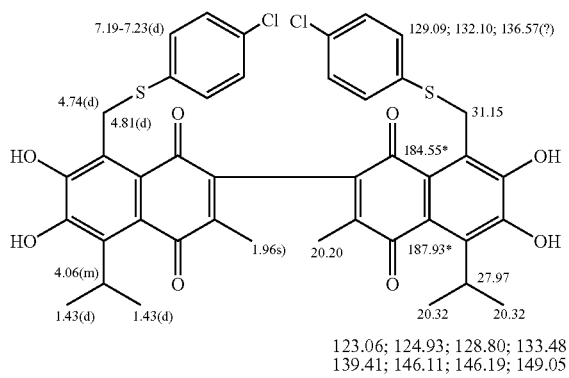

Example 7

Synthesis of 6,7,6',7'-tetrahydroxy-5,5'-diisopropyl-8,8'-bis-(2,3,5,6-tetrafluoro-phenylsulphanylmethyl)-3,3'-dimethyl-[2,2']binaphthalenyl-1,4,1',4'-tetraone (11)

The synthesis is essentially carried out as described in Example 3, the monothiol used being tetrafluorobenzenethiol.
Yield 60-70%
Mass spectrometry (ESI): 901 (M+Na)
IC50 (KB cell line)=$8.5 \times 10^{-6}$ M
The data for NMR $^1$H (on the left) and $^{13}$C (on the right) are shown in the formula (11):

(11)

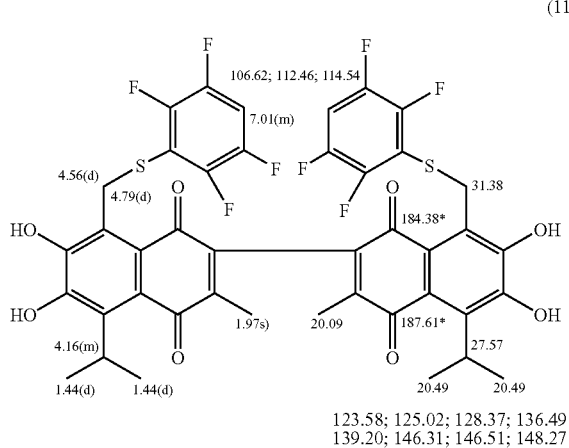

Example 8

Synthesis of 8,8'-bis-butylsulphanylmethyl-6,7,6',7'-tetrahydroxy-5,5'-diisopropyl-3,3'-dimethyl-[2,2']binaphthalenyl-1,4,1',4'-tetraone (12)

The synthesis is essentially carried out as described in Example 3, the monothiol used being thiobutane.
Yield 60-70%
Mass spectrometry (ESI): 693 (M–H)

The data for NMR $^1$H (on the left) and $^{13}$C (on the right) are shown in the formula (12):

(12)

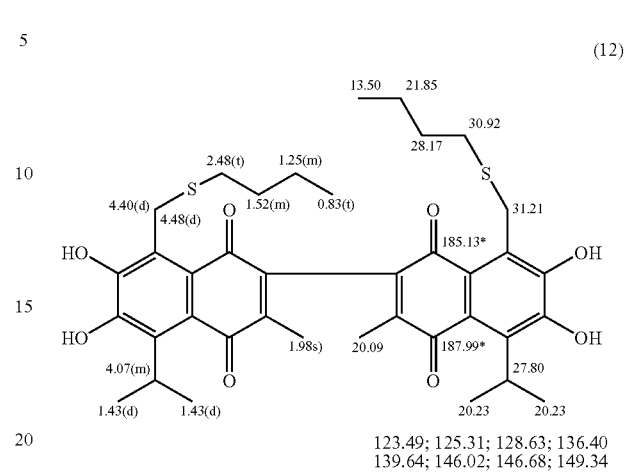

Alternatively, it is also possible to use thioethane in the place of thiobutane in order to produce 8,8'-bis-ethylsulphanylmethyl-6,7,6',7'-tetrahydroxy-5,5'-diisopropyl-3,3'-dimethyl-[2,2']binaphthalenyl-1,4,1',4'-tetraone (13)

(13)

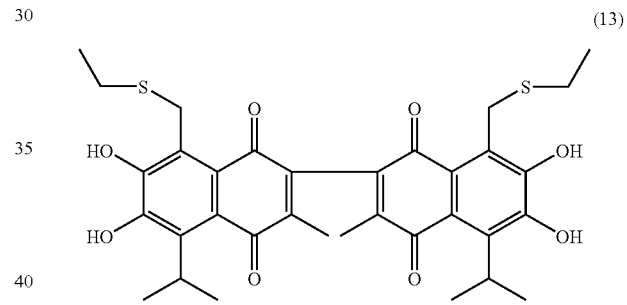

Example 9

Synthesis of 6,7,6',7'-tetrahydroxy-8,8'-bis-(2-hydroxy-ethylsulphanylmethyl)-5,5'-diisopropyl-3,3'-dimethyl-[2,2']binaphthalenyl-1,4,1',4'-tetraone (14)

The synthesis is essentially carried out as described in Example 3, the monothiol used being thioethanol.
Yield 60-70%
Mass spectrometry (ESI): 669 (M–H)
The data for NMR $^1$H (on the left) and $^{13}$C (on the right) are shown in the formula (14):

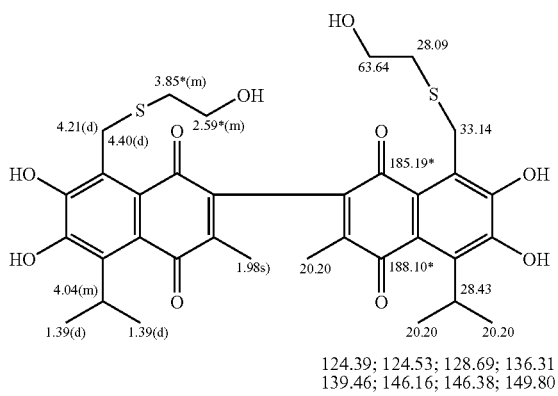

(14)

Example 10

Synthesis of a methylether derivative of the compound of formula (2), 6,7,6',7'-tetrahydroxy-8,8'-bis-methoxymethyl-5,5'-diisopropyl-3,3'-dimethyl-[2,2'] binaphthalenyl-1,4,1',4'-tetraone (6)

3 mol. eqv. of trifluoroacetic anhydride (TFAA) is added to a solution of 200 mg of the compound of formula (5) (0.36 mmole) in 10 ml of THF at 0° C. The mixture is stirred at 0° C. for 15 min, followed by evaporation in order to eliminate the THF. The reaction mixture is taken up in 10 ml of ether and 3 mol. eqv. of methylate (500 mg Na/10 ml MeOH) is added. After 5 hours, the reaction mixture is washed with water (3 times), then with saturated NaCl, dried over $Na_2SO_4$, and evaporated. The product is obtained by precipitation from ether and hexane.

Yield: 70%.

The data for NMR $^1$H (on the left) and $^{13}$C (on the right) are shown in the formula (6):

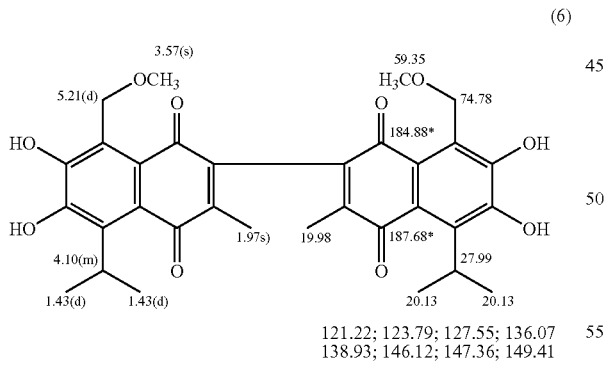

(6)

Example 11

Specific Inhibition of the Activity of Protein Kinases by the Compound of Formula (14)

The action of the compound of formula (14) was tested on a selection of 29 different protein kinases. The activity of these enzymes was measured in the presence of 10 μM of compound, according to the general methodology described by Bain et al. (2003) *Biochem. J.* 371:199-204 and Davies et al. (2000) *Biochem. J.* 351:95-105.

The results presented in Table 1 indicate that the compound of formula (14) specifically inhibits the activity of two enzymes, PRAK (kinase induced by glucocorticoids regulated/activated by p38) and SGK (kinase induced by glucocorticoids and serum), by reducing the activity of these enzymes by 91% and 93% respectively.

The SGK protein is known to be involved in regulation of the cell cycle and the inhibition of apoptosis (Buse et al. (1999) J. Biol. Chem. 274:7253-7263; Mikosz et al. (2001) *J. Biol. Chem.* 276: 16649-16654). It is therefore a preferred target in the context of combating cancer.

Example 12

Specific Inhibition of the Activity of Protein Kinases by the Compound of Formula (4)

The action of the compound of formula (4) was tested on a selection of 29 different protein kinases as described in Example 11.

The results shown in Table 1 indicate that the compound of formula (4) also inhibits, in a specific manner, the activity of two enzymes, PRAK (kinase induced by glucocorticoids and regulated/activated by p38) and SGK (kinase induced by glucocorticoids and serum), by reducing the activity of these enzymes by 91% and 96% respectively.

TABLE 1

| Protein kinase | Gossypol (10 μM) Residual activity | Gossypol (10 μM) Standard error | Gossypolone (10 μM) Residual activity | Gossypolone (10 μM) Standard error | Compound (14) (10 μM) Residual activity | Compound (14) (10 μM) Standard error | Compound (4) (10 μM) Residual activity | Compound (4) (10 μM) Standard error |
|---|---|---|---|---|---|---|---|---|
| MKK1 | 86 | 5 | 76 | 10 | 90 | 15 | 59 | 3 |
| MAPK2/ERK2 | 65 | 1 | 46 | 9 | 58 | 5 | 52 | 9 |
| JNK/SAPK1c | 90 | 2 | 86 | 10 | 88 | 12 | 105 | 2 |
| SAPK2a/p38 | 99 | 2 | 108 | 1 | 102 | 9 | 105 | 8 |
| SAPK2b/p38β2 | 125 | 8 | 102 | 3 | 113 | 13 | 124 | 4 |
| SAPK3/p38g | 108 | 15 | 83 | 9 | 76 | 4 | 89 | 9 |
| SAPK4/p38d | 66 | 9 | 75 | 15 | 85 | 15 | 88 | 15 |
| MAPKAP-K1a | 77 | 15 | 55 | 12 | 60 | 14 | 58 | 8 |
| MAPKAP-K2 | 56 | 4 | 28 | 2 | 36 | 9 | 28 | 1 |
| MSK1 | 79 | 15 | 85 | 9 | 83 | 15 | 69 | 2 |
| PRAK | 48 | 5 | 9 | 4 | 9 | 5 | 9 | 5 |
| PKA | 47 | 10 | 69 | 15 | 59 | 15 | 69 | 1 |
| PKCa | 96 | 1 | 78 | 6 | 86 | 1 | 85 | 12 |
| PDK1 | 71 | 4 | 51 | 15 | 65 | 4 | 88 | 10 |
| PKB?ph | 94 | 15 | 53 | 4 | 76 | 9 | 39 | 8 |
| SGK | 14 | 15 | 3 | 5 | 7 | 4 | 4 | 3 |
| p70 S6K | 110 | 1 | 35 | 5 | 52 | 9 | 34 | 6 |
| GSK3b | 47 | 2 | 43 | 5 | 85 | 4 | 63 | 7 |
| ROCK-II | 80 | 1 | 54 | 4 | 73 | 4 | 75 | 6 |
| AMPK | 72 | 13 | 66 | 4 | 70 | 7 | 61 | 7 |
| CHK1 | 9 | 6 | 24 | 15 | 47 | 15 | 127 | 9 |
| CK2 | 80 | 0 | 79 | 3 | 85 | 2 | 80 | 0 |
| PHK | 23 | 1 | 21 | 1 | 27 | 0 | 47 | 9 |
| Lck | 76 | 4 | 60 | 12 | 54 | 1 | 71 | 13 |
| CSK | 103 | 15 | 64 | 3 | 60 | 5 | 93 | 3 |
| CDK2/cyclin A | 97 | 1 | 90 | 12 | 111 | 10 | 113 | 7 |
| DYRK1a | 21 | 3 | 27 | 6 | 16 | 5 | 25 | 10 |
| CK1 | 89 | 5 | 64 | 9 | 77 | 2 | 88 | 1 |
| NEK6 | 92 | 15 | 89 | 8 | 81 | 4 | 86 | 12 |

Residual enzyme activity of protein kinases in the presence of inhibitor compounds at the concentration given (expressed as a percentage of the activity measured in the absence of inhibitors). The results obtained for gossypol and gossypolone are given by way of comparison.

The invention claimed is:

1. Compounds of general formula (1):

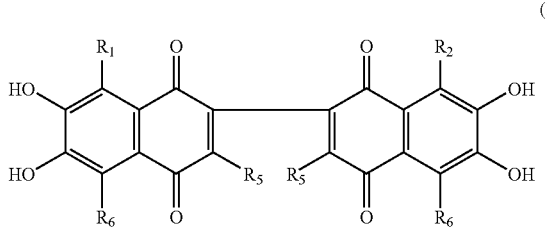

(1)

in which, independently of each other, $R_1$ and $R_2$ represent:
—OH, or
—$CH_2$—O—$R_3$, or
—$CH_2$—S—$R_3$, or

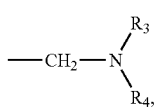

$R_3$, $R_4$, $R_5$ and $R_6$ representing, independently of each other, —H or a carbon-containing group with 1 to 10 carbon atoms, saturated or unsaturated, optionally comprising one or more heteroatomic groups.

2. Compounds according to claim 1, of general formula (1) in which, independently of each other, $R_3$, $R_4$, $R_5$ and $R_6$ represent:
—H, an alkyl group, a heteroalkyl group, such as a thioalkyl, a hydroxyalkyl, an aminoalkyl, a halogenoalkyl or an alkoxyalkyl, a cycloalkyl group, an alkenyl group, a heteroalkenyl group, an aryl group, a heteroaryl group, such as a thioaryl, a hydroxyaryl, an aminoaryl, a halogenoaryl or an alkoxyaryl or an arylalkyl group.

3. Compounds according to claim 1, of general formula (1) in which $R_5$ and $R_6$, independently of each other, represent an alkyl group with 1 to 8 carbon atoms.

4. Compounds according to claim 1, of general formula (1) in which $R_1$ and $R_2$ are identical.

5. Compounds according to claim 1, of general formula (1) in which $R_5$ represents a methyl group and $R_6$ represents an isopropyl group.

6. Compounds according to claim 1, of general formula (2):

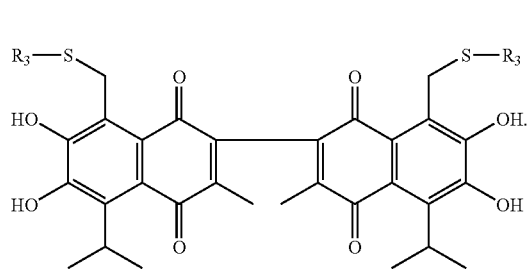
(2)

in which $R_3$ represents —H or a carbon-containing group with 1 to 10 carbon atoms, saturated or unsaturated, optionally comprising one or more heteroatomic groups.

7. Compounds according to claim 1, of general formula (3):

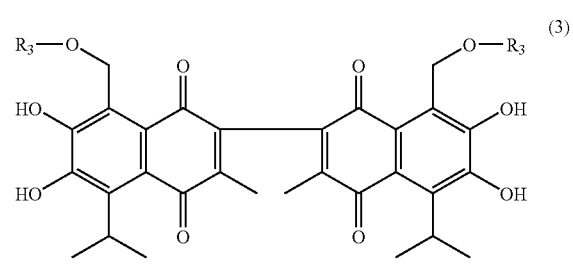
(3)

in which $R_3$ represents —H or a carbon-containing group with 1 to 10 carbon atoms, saturated or unsaturated, optionally comprising one or more heteroatomic groups.

8. Compounds according to claim 1, of the following formula:

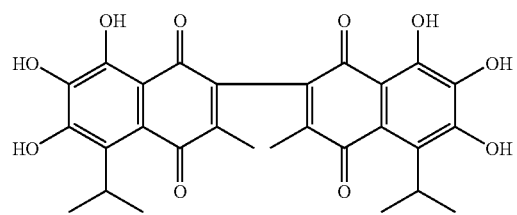
(4)

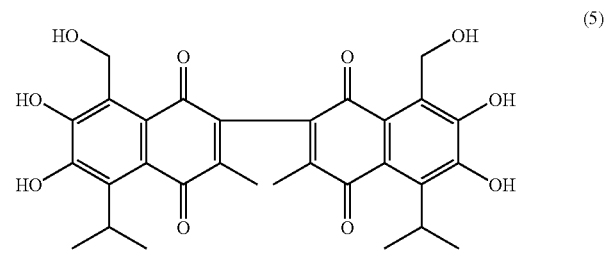
(5)

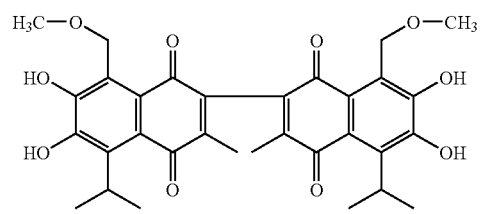
(6)

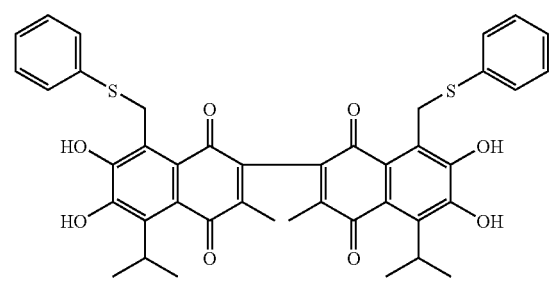
(7)

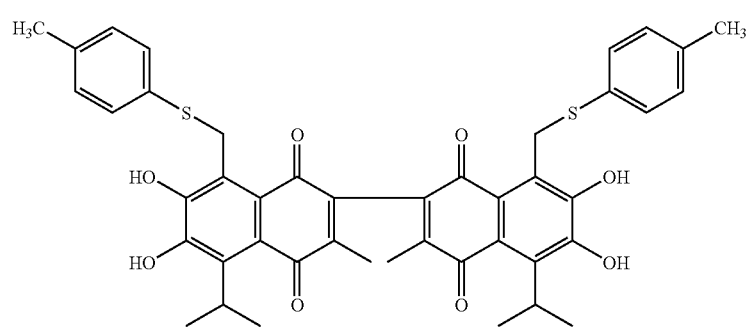
(8)

-continued
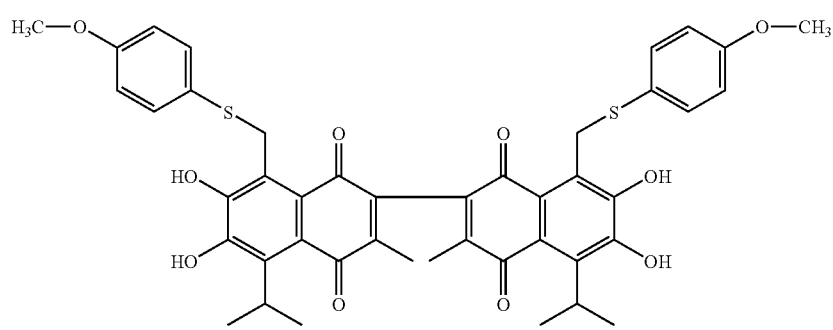
(9)
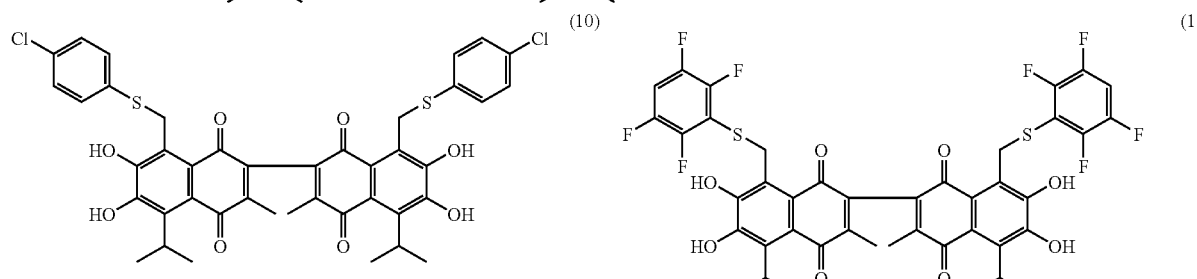
(10) (11)
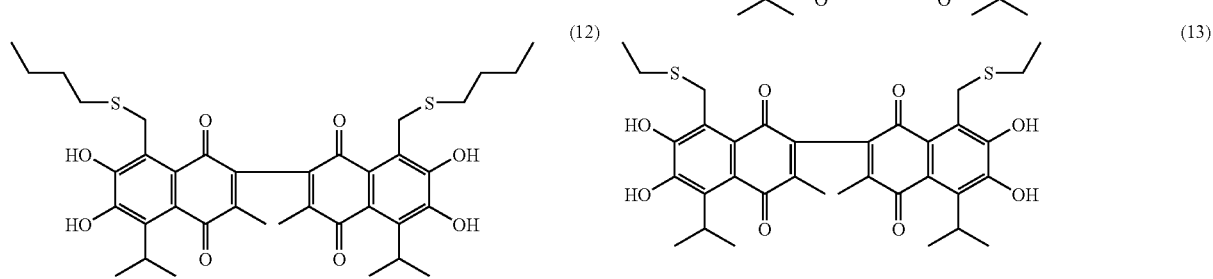
(12) (13)
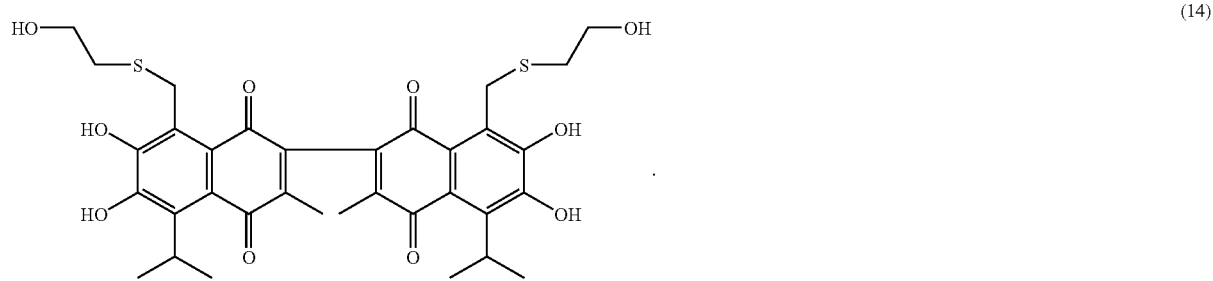
(14)
9. Pharmaceutical composition comprising as active ingredient at least one compound as defined in claim 1, or their pharmaceutically acceptable salts.
10. Pharmaceutical composition comprising as active ingredient the compound (4) and/or the compound (14), as defined in claim 8.
* * * * *